United States Patent [19]

D'Angelo et al.

[11] 3,965,145

[45] June 22, 1976

[54] COUPLED PEROXIDES

[75] Inventors: Antonio Joseph D'Angelo, Englishtown, N.J.; Orville Leonard Mageli; Chester Stephen Sheppard, both of Kenmore, N.Y.

[73] Assignee: Pennwalt Corporation, Philadelphia, Pa.

[22] Filed: Jan. 16, 1974

[21] Appl. No.: 433,945

Related U.S. Application Data

[60] Continuation-in-part of Ser. No. 342,111, March 16, 1973, abandoned, which is a division of Ser. No. 737,359, June 17, 1968, Pat. No. 3,725,455.

[52] U.S. Cl. .................. 260/471 C; 260/46.5 G; 260/75 T; 260/77.5 A; 260/77.5 B; 260/77.5 D; 260/455 R; 260/463; 260/468 E; 260/479 S; 260/482 B; 260/485 R; 260/485 G; 260/557 R; 260/557 B; 260/558 R; 260/561 R; 260/561 B; 260/611 R; 260/861; 260/961; 526/213; 526/215; 526/339; 526/340; 526/346; 260/963
[51] Int. Cl.² ............... C07C 179/18; C07C 179/20
[58] Field of Search......... 260/471 C, 482 B, 468 E, 260/463, 485 G

[56] References Cited
UNITED STATES PATENTS 3,725,455  4/1973  D'Angelo et al..................... 260/463
3,783,152  1/1974  Larsen ............................ 260/471 C
3,839,390  10/1974  D'Angelo et al................ 260/453 R

*Primary Examiner*—James A. Patten

[57] ABSTRACT

A new class of compounds: R—W—R' were R and R' are identical oxy radicals containing peroxide functions such as dialkyl or diaralkyl peroxide, peroxyketal, peroxyester, or monoperoxycarbonate, and W is a carbonyl group, or carbonyl containing group, or an alkylidene or aralkylidene group, or a phosphorus containing group.

Examples

Di[1,3-dimethyl-3-(t-butylperoxy)butyl]carbonate;
Di[1,3-dimethyl-3-(n-butoxycarbonylperoxy)butyl]-carbonate;
2,2-Bis[3,3-di(t-butylperoxy)butoxy]propane;
Di[1,3-dimethyl-3-(t-butylperoxy)butyl]ethyl phosphate.

They are free radical affording compounds useful in crosslinking of polyolefins and unsaturated polymers, and for the polymerization of vinyl monomers and diolefinic monomers.

5 Claims, No Drawings

COUPLED PEROXIDES

RELATED APPLICATIONS

This application is a continuation in-part of application Ser. No. 342,111, filed Mar. 16, 1973, now abandoned, which in turn is a division of application Ser. No. 737,359, filed June 17, 1968 (now U.S. Pat. No. 3,725,455).

BACKGROUND OF THE INVENTION

1. The Field of the Invention

This invention relates to peroxides obtainable by the coupling of hydroxide group containing peroxides. Particularly the invention relates to coupled peroxide containing one or more carbonyl groups or an alkylidene group in the portion of the molecule which forms the linkage between the two peroxy containing portions of the coupled peroxide coupled Also the invention relates to methods for preparing such coupld peroxides.

2. Description of Related Art

U.S. Pat. No. 3,236,872 discloses dialkyl peroxides containing hydroxyl groups, e.g., 2-methyl-2-(t-butylperoxy)-4-pentanol.

A copending application, Ser. No. 569,030, filed Aug. 1, 1966 (now U.S. Pat. No. 3,542,856) discloses peroxyesters containing hydroxyl groups, e.g., t-butylperoxy-3-hydroxypropionate.

Still other precursors, hydroxy substituted peroxyketals are disclosed in a copending application, Ser. No. 727,336 filed May 7, 1968, now U.S. Pat. No. 3,853,957, e.g., 3,3-Bis(t-butylperoxy)-1-butanol.

SUMMARY OF THE INVENTION

It has been discovered that high purity polyfunctional peroxides, i.e., at least two peroxy groups, can be prepared by a coupling reaction carried out on a hydroxy containing peroxide.

The novel polyfunctional peroxides of this invention have the general formula:

$$R-W-R'$$

where:
1. R and R' are identical, and each contains at least one peroxy (—OO—) group selected from:

(i)   $R_3OO-C(R_1)(R_2)-R^3-O-$, (ii)  $(R_3OO)_2C(R_4)-R^2-O-$, (iii) $R_3OO-C(=O)-R^3-O-$, (iv) $R_3OOC(=O)-O-R^3-O-$, (v)  $R_1OC(=O)-OO-C(R_1)(R_2)-R^2-O-$ and (vi) $R_1C(=O)-OO-C(R_1)(R_2)-R^2-O-$, where R and R' each fall into the same member (i)–(vi) respectively and the $R_1$, $R_2$, $R_3$, $R_4$, $R^2$, $R^3$, and $R^4$ required to be present in the particular R' is the same as the corresponding radical [i.e., $R_1$, $R_2$, $R_3$, $R_4$, $R^2$, $R^3$, and $R^4$ as the case may be ] required to be present in the corresponding R. To illustrate: If R is: $R_1-C(=O)-OO-C(R_1)(R_2)-R^2-O-$, then R' is also $R_1-C(=O)OO-C(R_1)(R_2)-R^2-O-$, and $R_1$, $R_2$, and $R^2$ are identical in both R and R';

2. W is a diradical selected from (i)   $-C(=O)-$, (ii)  $-C(=O)C(=O)-$, (iii) $-C(=O)R^4C(=O)-$, (iv) 

and (v)  $R_7-\overset{|}{\underset{|}{C}}-R_8$;

3. $R_1$ and $R_2$ are aliphatic having 1–12 carbon atoms, cycloaliphatic having 3–12 carbon atoms, or aromatic having 6–12 carbon atoms (preferably $C_1$–$C_{12}$ hydrocarbon aliphatic);

4. $R_3$ is aliphatic or cycloaliphatic, each having 4–10 carbon atoms (preferably $C_4$–$C_{10}$ hydrocarbon aliphatic) and the carbon atoms joined to the peroxy oxygen atom is a tertiary carbon atom;

5. $R_4$ is aliphatic having 1–10 carbon atoms or cycloaliphatic having 3–12 carbon atoms (preferably $C_1$–$C_{10}$ hydrocarbon aliphatic);

6. $R_5$ is lower alkyl, cycloalkyl, aralkyl, aryl, alkoxy, cycloalkoxy, aralkoxy, or aryloxy;

7. $R_6$ is H or lower alkyl;

8. Y is the diradical $-O-$, $-S-$ or $-N(R_6)-$;

9. $R^2$ is an aliphatic diradical having 1–10 carbon atoms or a cycloaliphatic diradical having 3–12 carbon atoms (preferably $C_1$–$C_{10}$ hydrocarbon aliphatic);

10. $R^3$ is an aliphatic diradical having 1–10 carbon atoms, cycloaliphatic diradical having 3–12 carbon atoms, or aromatic diradical having 6–12 carbon atoms, with the proviso that $R^3$ is not aromatic when W is $-C(=O)R^3C(=O)-$;

11. $R_7$ and $R_8$ are selected from the class consisting of H, alkyl of 1 – 10 carbons and cycloalkyl of 3–12 carbons and when $R_7$ is H, $R_8$ can also be aryl of 6–12 carbons and $R_7$ and $R_8$ can together form an alkylene biradical of 2–11 carbons; and 12. $R^4$ is a diradical selected from (i)    $R^3$, (ii)   $YR^3Y$, (iii)  $R^3C(=O)YR^3YC(=O)R^3$, (iv)  $YR^3YC(=O)YR^3YC(=O)YR^3Y$, (v)   $YR^3YC(=O)R^3C(=O)YR^3Y$, (vi)  $YR^3C(=O)YR^3YC(=O)R^3Y$, (vii)  $YR^3C(=O)YR^3C(=O)YR^3Y$, (viii) $YR^3YC(=O)YR^3Y$, (ix)  $YR^3YC(=O)R^3Y$ and (x)   $YR^3YR^3Y$, especially $R^3$, $YR^3Y$, $YR^3OC(=O)R^3C(=O)OR^3Y$, $YR^3OC(=O)R^3Y$ and $YR^3OR^3Y$.

Illustrative peroxides are:

Di[1,3-dimethyl-3-(t-butylperoxy)butyl] carbonate;
Di[4,4-di(t-butylperoxy)pentyl] carbonate;
Di[1,3-dimethyl-3-(t-butylperoxy)butyl] succinate;

Ethylene Bis[1,3-dimethyl-3-(t-butylperoxy)-butyl carbonate];

Di[1,3,-dimethyl-3-(t-butylperoxy)butyl] ethyl phosphate;

2,2-Bis[3,3-di(t-butylperoxy)butoxy]propane;

N,N'-m-phenylene bis [1,3-dimethyl-3-(t-butyl-peroxy)butyl carbamate];

N,N'-(4-methyl-1,3-phenylene)bis[1,3-dimethyl-3-(t-butylperoxy) butyl carbamate];

N,N'-hexamethylene bis[1,3-dimethyl-3-(t-butylperoxy)butyl carbamate];

N, N', N, N'-diethylene bis[1,3-dimethyl-3-(t-butylperoxy) butyl carbamate];

Ethylene bis[1,3-dimethyl-3-(t-butylperoxy)-butyl carbamate];

Di-(2,2-di-(t-butylperoxy)propyl)sebacate; and 2,4-Di-[2-methyl-3,3-di-(t-butylperoxy)-butoxycarbonylamino] toluene.

DESCRIPTION OF THE INVENTION AND EXAMPLES

The aliphatic radical includes substitution by aryl radicals -- araliphatic radicals -- and cycloaliphatic radicals. The cycloaliphatic radical includes substitution by aliphatic and by aryl radicals. The aromatic and aryl radicals may be substituted by aliphatic and by cycloaliphatic radicals. Both cycloaliphatic, aromatic and aryl radicals may be single ring, such as phenyl and cyclohexyl, or connected rings, such as biphenyl, binaphthyl, bicyclopropyl, bicyclopentyl, or fused rings such as naphthyl, decahydronaphthyl. It is to be understood that the substituents should not interfere with the desired coupling reaction. In general halogen, ester, ether, thioether, and carbonate substituents or groups containing these do not interfere. Desirably $R_1$, $R_2$, $R_3$, $R_4$, $R^2$, $R^3$, and $R^4$ contain only carbon and hydrogen atoms.

Commonly $R_5$ is alkyl or alkoxy having 1–6 carbon atoms; cycloalkyl or cycloalkoxy having a total of 3–12 carbon atoms; aralkyl or aralkoxy having 7–12 carbon atoms; aryl or aryloxy having 6–12 carbon atoms.

Commonly, $R_6$ is H or alkyl having 1–4 carbon atoms.

Commonly $R_7$ and $R_8$ are each H or alkyl having 1–4 carbon atoms or one can be aryl while the other is H or $R_7$ and $R_8$ together can form an alkylene biradical.

$R_3$ is an aliphatic or cycloaliphatic radical, each having 4–10 carbon atoms, affording a t-carbon which is joined to a peroxy oxygen atom. For example:

polybutene-styrene copolymers and urethane rubber), copolymers such as poly-(ethylene-vinyl acetate) and condensation polymers such as polyamides, polyesters (both saturated and unsaturated) and polycarbonates. The polymer may contain a plasticizer and/or oil extenders and/or fillers such as carbon black, silica and calcium carbonate. Also they are effective in curing (crosslinking) mixtures of vinyl monomers and unsaturated polyesters.

Also they are effective for the polymerization, to form solid polymers, of unsaturated monomers capable of polymerization by a free radical mechanism. For example, vinyl monomers such as vinyl halides; vinylidene halides, vinyl esters such as vinyl acetate and vinyl stearate; the vinyl toluene; the acrylics such as acrylic acid, methyl methacrylate and ethyl acrylate. Other monomers are: The styrene-butadiene blends for rubber copolymers; styrene-acrylonitrile blends for copolymers; fluoroethylenes and chloro-fluoroethylenes; butadiene; isoprene and similar polymerizable dienes.

UTILITY AND DISCUSSION

These novel coupled peroxycompounds can be utilized in the following ways:

1. They can crosslink polyethylene, polyethylene-polypropylene rubber, polyolefin elastomers, uretahane rubbers, silicon rubber, etc. (Example XV, Tables I, II, III and IV)

2. They can polymerize monomers containing polymerizable ethylenic grouping. (Example XVI)

3. They can cure resins curable by free radical producing agents. (Example XVII)

4. They can be used as free radical sources and/or catalysts in organic syntheses and applications where free radicals are required.

Some of the desirable properties that a peroxide has to have to be useful for crosslinking polyethylene are: low volatility, high thermal stability, and good efficiency with respect to its active oxygen content.

The volatility and the thermal stability are necessary requisites, since the peroxide has to tolerate the high temperatures of the milling operation, which is a necessary step to incorporate the peroxide with the polymer before the crosslinking process. If the peroxide is too volatile (as in the case of di-t-butyl peroxide) there would not be any peroxide left for the crosslinking process at the end of the milling step. If the peroxide is not volatile, but its thermal stability is low, a premature

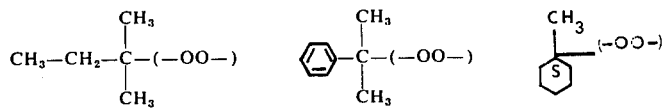

The described coupled peroxy compounds are effective crosslinking agents for polymeric materials which are capable of being crosslinked to form a thermoset material.

Illustrative classes of polymeric materials where these new peroxy compounds are effective include: homopolymers, such as poly(vinyl chloride) and polyolefins (e.g. polyethylene and polybutenes); elastomers, such as natural rubber and synthetic rubber (e.g. butyl rubber, GR-S rubbers, neoprene, acrylic rubber, Buna rubber, ethylene-propylene rubber, silicone rubbers, and miscellaneous elastomeric material such as decomposition of the peroxide will take place during the milling step, which results in a premature crosslinking of the polymer. If this happens, the polymer cannot be shaped or formed any further since the thermoplastic polymer has become thermoset too soon.

Efficiency is another property that a good crosslinking peroxide has to have in order to make the crosslinking process economical and effective.

Another advantage of the difunctional peroxides obtained by the coupling reaction is that they utilize their active oxygen content to the full extent. Some of the known commercial difunctional peroxides like 2,5- dimethyl-2,5-di(t-butylperoxy)hexane and 2,5-dimethyl-2,5-di(t-butylperoxy)-hexyne-3 are not as efficient in utilizing their active oxygen content as the difunctional peroxide of our invention (see Table I). This is an unexpected result.

We have demonstrated that hydroxy containing peroxides, such as 2-methyl-2-(t-butylperoxy)-4-pentanol, do not have all the desirable properties of a good crosslinking agent. Its volatility is low and its thermal stability is good, but its efficiency is poor. (see Table I)

By coupling this hydroxy containing peroxide, using the process described in Examples I, II, and III, we found the coupled product to be an exceptionally good crosslinking agent possessing all the desirable properties. (see Table I)

The half-life of the coupled products (e.g. from Examples I, II, III, and V) is almost double that of the hydroxy containing peroxide precursors. This, to say the least, is unexpected. (see Example XVIII)

Another advantage of the coupling reaction is the simplicity of preparing pure difunctional peroxides without going through tedious purification steps that are necessary when they are prepared by peroxidizing difunctional intermediates.

The coupling reaction is not the only expedient one can use to improve volatility of the hydroxy containing peroxides. One can acylate the hydroxyl group with a sufficiently high molecular weight acylating agent and the volatility will be reduced. Using too low of a molecular weight acylating agent will not lower volatility sufficiently unless the starting hydroxy-containing peroxide is already of substantial molecular weight.

The disadvantage of this approach is that an increase in the molecular weight of the peroxide is attained at a sacrifice of active oxygen content.

Peroxides are sold by the pound and used according to the active oxygen content. So, if one had to buy a high molecular weight product with small active oxygen content, larger amounts of the product would have to be used to obtain the desired results in that particular application.

The coupled compounds of our invention minimize this disadvantage, since they give the desirable properties without excessively increasing the molecular weight.

Thus, the coupling reactions of hydroxy-containing peroxides R—H, afford novel peroxides, R—W—R', that are unexpectedly more stable than R—H; more efficient than R—H and other commercial diperoxides; and at the same time are less volatile than R—H and simple derivatives of R—H.

PREPARATION

Hydroxy-containing peroxide precursors, R—H, can be prepared by peroxidation of intermediates containing hydroxyl groups, either primary or secondary, or by hydrolysis or reduction of ester-containing peroxides.

Peroxides, R—W—R', of this invention may be prepared by reacting the hydroxy-containing peroxides, R—H, with hydroxy coupling agents such as phosgene, diacid chlorides, bischloroformates, diisocyanates, dichlorophosphonates, aldehydes, and ketals.

Peroxides of this invention may be prepared, for example, by one or more of the following methods.

Method I (The One Step Process)

Two moles of the hydroxy-containing peroxide are reacted with one mole of the desired hydroxy-coupling agent to obtain R—W—R'.

Illustrative reactions are:

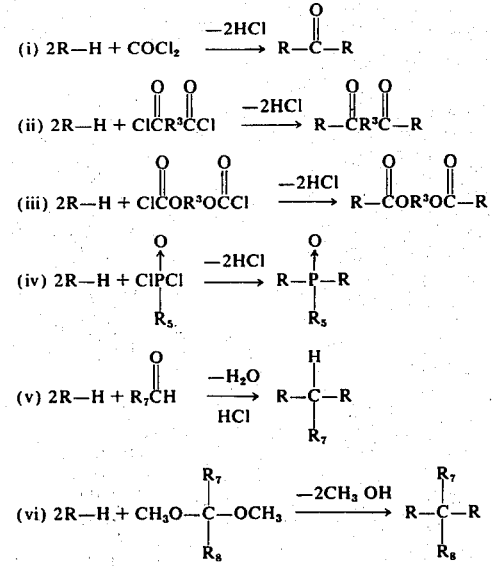

Method II (The Two Step Process)

One mole of the hydroxy-containing peroxide is first reacted with one mole of hydroxy coupling agent to attain an intermediate product.

The preparation of certain of these intermediate products is discosed in copending application Ser. No. 727,323 filed May 7, 1968 (now U.S. Pat. No. 3,671,651).

This intermediate product can subsequently be reacted with another mole of the hydroxy-containing peroxide in a second step to form R—W—R'.

Illustrative reactions are:

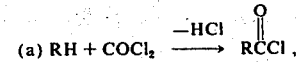

followed by

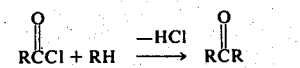

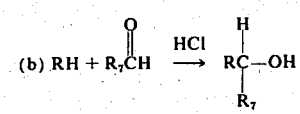

followed by

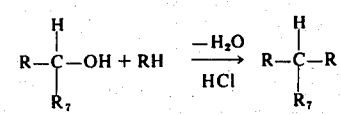

In other illustrative reactions when the intermediate product is a chloroformate-, or acid choride-, or isocyanate-, or chlorophosphonate-containing peroxide, the intermediate can be reacted with other difunctional compounds such as diamines, diols, and dimercaptans in the second step to form R—W—R':

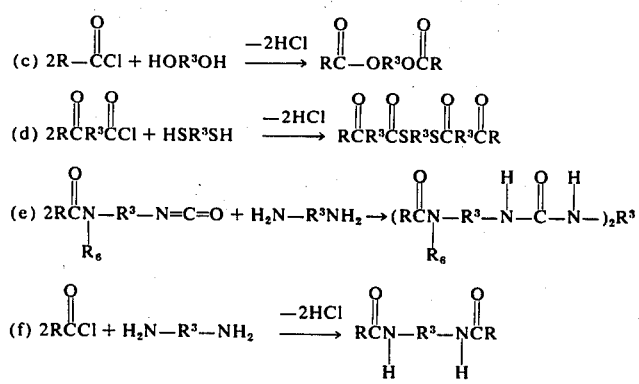

When the intermediate product is a chloroformate-containing peroxide, it can also be converted directly to R—WR' in the second step, e.g.

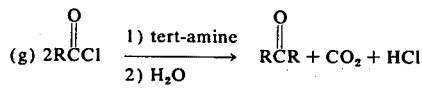

The reaction conditions depend upon the characteristics of the reactants and peroxy products. In general the intermixing of the coupling agent and the peroxy compound is carried out from about −10° to +25°C., and then the reaction temperature may be increased to a maximum of not more than 100°C., to allow the reaction to go to completion. Preferably the maximum reaction temperature should be not more than about 60°C.

The reactions may take place in the presence or absence of an inert diluent or solvent. In certain cases, where one or more of the reactants are solids, such a diluent is necessary to provide intimate contact of the reactants; in other cases the diluent provides an additional safety factor, as some pure products are hazardous.

In certain cases the presence of a base may be necessary i.e. Method I (i), (ii), (iii), and (iv) or method II (a), (c), (d), and (f).

Any compound, inorganic or organic in nature, which functions as an acid acceptor (base) for the acid by-product of the reaction can be used.

Illustrative of organic bases are: pyridine, and substituted pyridines; lower alkyl tertiary amines such as trimethyl amine, and triethylamine; dimethyl aniline; and N-methyl-2-pyrrolidone.

Illustrative inorganic bases which can be used are the basic salts of alkali metals and alkaline earth metals such as sodium, and potassium carbonates, and sodium and potassium hydroxide.

Methods of preparation of the novel peroxides, R—W—R', are further illustrated in Examples I to XIV.

EXAMPLE I

Preparation of Di[1,3-dimethyl-3-(t-butylperoxy)butyl]carbonate [A]

To a mixture of 22.6 g. (0.1 mole) of 2-methyl-2-(t-butylperoxy)-4-pentanol (84%) and 15.8 g. (0.2 mole) of pyridine in 50 ml. of hexane cooled to 5° ± 1°C. was added a solution of 5 g. (0.05 mole) of phosgene in 50 ml. of hexane.

The addition was made at such rate that the reaction temperature could be controlled at 5° ± 1°C. After the addition was completed, the reaction temperature was allowed to rise to 23°–25°C., and then raised to 50° ± 1°C. by means of external heating. The reaction mixture was allowed to react for 48 hours at this temperature.

The reaction mixture was filtered from the pyridine hydrochloride and the organic phase washed with 10% tartaric acid solution and water to neutrality.

The organic phase was then dried over anhydrous magnesium sulfate, filtered and the solvent evaporated under reduced pressure. A slightly colored liquid was obtained, 20.1 g., theoretical 20.3 g. The infrared spectrum (I.R.) of this material showed presence of trace amounts of unreacted 2-methyl-2-(t-butylperoxy)-4-pentanol.

The unreacted material was distilled under reduced pressure at 34°–35°C. and .05 mm. of Hg. The I.R. of the residue was free of OH and contained the characteristic bands of the desired product.

EXAMPLE II

Preparation of [A]

To a solution of 27.2 g. (0.1 mole) of 1,3-dimethyl-3-(t-butylperoxy) butyl chloroformate (93.5%) (prepared from 2-methyl-2-(t-butylperoxy)-4-pentanol and phosgene) in 75 ml. of diethyl ether, cooled at 15°± 1°C. was added a solution of 7.9 g. (0.1 mole) of pyridine in 25 ml. diethyl ether. The pyridine chloroformate complex separated at first and then dissolved, giving a pink colored solution. While the reaction temperature was controlled 15° ± 1°C., a solution of 22.6 g. (0.1 mole) of 2-methyl-2-(t-butylperoxy)-4-pentanol (84%) in 50 ml. of diethyl ether was added dropwise.

After the addition was completed, the mixture was allowed to reflux for twenty-four hours at 36° ± 1°C. At the end of this period the reaction mixture was filtered from the pyridine hydrochloride and washed with 10% solution of tartaric acid and water to neutrality. The ether solution was dried over anhydrous MgSO₄, filtered and the solvent evaporated under reduced pressure and then under vacuum at 0.1 mm. of Hg and a bath temperature of 60° to 70°C. A liquid was obtained (40 g.); theoretical yield 40.6 g.

The I.R. of this liquid was free of OH and C—Cl bands and contained the characteristic bands of the desired product.

EXAMPLE III

Preparation of [A]

To a solution of 29.2 g. (0.1 mole) of 1,3-dimethyl-3-(t-butylperoxy) butyl chloroformate (86.5%) in diethyl ether at 23° ± 1°C. was added a solution of 7.9 g. (0.1 mole) of pyridine in 10 ml of diethyl ether. To this mixture was added dropwise 0.6 g. of $H_2O$ at such a rate that the evolution of $CO_2$ could be controlled to a reasonable rate. The reaction temperature rose to about 30°C. The reaction mixture was allowed to react at room temperature (23°C.) until the $CO_2$ evolution ceased (24 hours). The reaction mixture was diluted with $H_2O$ and the organic phase was separated, washed with 10% solution of tartaric acid and $H_2O$ to neutrality.

The ether solution was dried over anhydrous $MgSO_4$, filtered and the solvent evaporated under reduced pressure and then under vacuum at 0.1 mm. of Hg. and a bath temperature of 60°–70°C. A liquid was obtained 16.2 g.; theoretical yield 20.3 g.

The I.R. of this material was free of OH and C—Cl bands and contained the characteristic bands of the desired product.

EXAMPLE IV

Preparation of Di[4,4-di(t-butylperoxy)pentyl] carbonate

To a mixture of 8.0 g. (0.0295 mole) of 4,4-di(t-butylperoxy)-5-pentanol (97.3%), 2.4 g. (0.0295 mole) of pyridine in 50 ml. diethyl ether cooled at 5° ± 1°C. was added a solution of 1.45 g. (0.0147 mole) of phosgene in 25 ml. of diethyl ether. After the addition was completed, the reaction mixture was allowed to stir for 6 hours at 23° ± 1°C. After this time, the pyridine hydrochloride was filtered off and the ether solution was washed with 10% solution of tartaric acid and water to neutrality. The ether phase was dried over anhydrous $MgSO_4$, filtered and the solvent evaporated under reduced pressure. A liquid was obtained, 8.5 g.

The I.R. indicated that the desired product was obtained.

EXAMPLE V

Preparation of Di[2-(t-butylperoxycarbonyl)ethyl] carbonate [B]

To a mixture of 17.4 g. (0.1 mole) of t-butyl 3-hydroxyperoxypropionate (93%) and 7.9 g. (0.1 mole) of pyridine in diethyl ether cooled as 5° ± 1° C. was added a solution of 30.5 g. (0.1 mole) of 2-(t-butyl-peroxycarbonyl)-ethyl chloroformate (75%) in 50 ml. of diethyl ether.

After the addition was completed the reaction mixture was allowed to stir for one hour at 30°± 1°C. After the end of this period the reaction mixture was filtered off from the pyridine hydrochloride and the ether solution was washed with 10% solution tartaric acid and water to neutrality. The ether solution was dried over anhydrous $MgSO_4$, filtered and the solvent evaporated under reduced pressure. A colorless liquid was obtained (41 g.). The I.R. of this material showed the characteristic bands for the desired product.

EXAMPLE VI

Preparation of Di[1,3-dimethyl-3-(n-butoxycarbonylperoxy)-butyl] carbonate

To a mixture of 26.0 g. (0.1 mole) of O,O-(1,1-dimethyl-3-hydroxybutyl) O-butyl monoperoxycarbonate (90%) and 7.9 g. (0.1 mole) of pyridine in 50 ml. of diethyl ether, cooled at 10° ± 1°C. was added a solution of 31.4 g. (0.1 mole) of 1,3-dimethyl-3-(n-butoxycarbonylperoxy)butyl chloroformate in 50 ml. of diethyl ether, at such a rate that the reaction could be controlled at 10° ± 1°C.

After the addition was completed, the reaction temperature was allowed to rise to 23°–25°C. and allowed to stir for one hour. At the end of this time, the reaction mixture was diluted with water and the organic phase separated and washed with 10% solution of tartaric acid and water to neutrality. The ether phase was dried over anhydrous magnesium sulfate, filtered and the solvent evaporated under reduced pressure and then under vacuum of 30° to 35°C. and 0.05 mm. of Hg. A liquid was obtained, 45.3 g.

The I.R. of this material indicated that the desired product was prepared.

EXAMPLE VII

Preparation Di[1,3-dimethyl-3-(t-butylperoxy)butyl] succinate

A mixture of 4.13 g. (0.02 mole) of 2-methyl-2-(t-butylperoxy)-4-pentanol (92%) and 1.5 g. (0.01 mole) of succinyl chloride and 25 ml. of diethyl ether was refluxed for 48 hours.

Evolution of hydrochloric acid could be detected as the mixture was refluxing. At the end of 48 hours no more HCl could be detected.

The mixture was stripped under reduced pressure. A slightly yellow colored liquid was obtained weighing 4.4 g.; theoretical yield 4.42 g.

The I.R. of this material was free of OH and C—Cl bands and contained the characteristic bands of the desired product.

EXAMPLE VIII

Preparation of Ethylene Bis[1,3-dimethyl-3-(t-butylperoxy)-butyl carbonate]

To a mixture of 29.4 g. (0.1 mole) of 1,3-dimethyl-3-(t-butylperoxy)butyl chloroformate (86.3%) and 3.6 g. (0.05 mole) of ethylene glycol in 26 ml. of acetone and 25 ml. of diethyl ether at 20° ± 1°C. was added a solution of 7.9 g. (0.1 mole) of pyridine in 10 ml. of diethyl ether. The mixture was allowed to react for 24 hours at 25° ± 1°C. At the end of this period the reaction mixture was filtered off from the pyridine hydrochloride and the organic phase washed with 100 ml. 10% solution of tartaric acid and water to neutrality. The ether solution was dried over anhydrous $MgSO_4$, filtered and the solvent evaporated under reduced pressure.

A yield of 15.2 g. was obtained. The I.R. of this material showed the characteristic bands of the desired compound with little contamination of hydroxyl-containing material.

EXAMPLE IX

Preparation of
Di[1,3-dimethyl-3-(t-butylperoxy)butyl] ethyl phosphate

To a mixture of 22.1 g. (0.1 mole) of 2-methyl-2-(t-butylperoxy)-4-pentanon (86%) and 7.9 g. (0.1 mole) of pyridine in 50 ml. of diethyl ether cooled at 5° ± 1°C. was added a solution of 8.14 g. (0.05 mole) of ethyl dichlorophosphonate in 10 ml. of diethyl ether.

After the addition was completed the reaction mixture was allowed to stir at 25° ± 1°C. for 24 hours.

At the end of this time the reaction mixture was filtered from the pyridine hydrochloride and it was washed with 10% solution of tartaric acid and water to neutrality. The ether solution was dried over anhydrous $MgSO_4$, filtered and the solvent evaporated under reduced pressure. A liquid was obtained (13 g.). The I.R. indicated that the desired product was prepared.

EXAMPLE X

Preparation of N,N'-m-phenylene bis[1,3-dimethyl-3-(t-butyl-peroxy)butyl carbamate]

A mixture of 4.2 g. (0.02 mole) of 1,3-dimethyl-3-(t-butylperoxy) butanol (91%) and 1.6 g. (0.01 mole) of m-phenylenediisocyanate and few crystals of triethylamine diamine and 40 ml. of hexane was placed into a dry flask, equipped with magnetic stirrer, thermometer, condenser and drying tube.

The mixture was allowed to stir for four hours at 50° to 60°C. At the end of this time the reaction mixture contained an insoluble organic material.

This material was separated and the trace amount of solvent stripped under reduced pressure. A viscous liquid weighing 1.8 g. was obtained. The I.R. indicated that the desired product was obtained.

EXAMPLE XI

Preparation of 2,2-bis[3,3-di(t-butylperoxy)butoxy] propane

A mixture of 21.0 g. (0.08 mole) of 3,3-di(t-butylperoxy)butanol (96.6%), 4.2 g. (0.04 mole) of 2,2-dimethoxypropane, 25 ml. of benzene and 0.002 g. of p-toluenesulfonic acid were combined and the mixture was distilled under atmospheric pressure. When 13 ml. of distillate boiling from 57° to 59°C. was collected, the distillation was stopped.

The pot reside was cooled down to 23° to 25°C. and neutralized with anhydrous $Na_2CO_3$. The mixture was filtered and the remaining solvent evaporated under reduced pressure. A liquid weighing 19.2 g. was obtained. The I.R. indicated that the desired product was prepared.

EXAMPLE XII

Preparation of
Bis(2[1,3-dimethyl-3-(t-butylperoxy)butoxy-carboxamido]ethyl) fumarate A mixture of 4.2 g. (0.2 mole) of 1,3-dimethyl-3-(t-butylperoxy)-4-pentanol and 2.5 g. (0.01 mole) of bis(2-isocyanoethyl) fumarate and 100 ml. of hexane was placed into a dry flask equipped with magnetic stirrer, thermometer, condenser and drying tube.

The mixture was allowed to stir for 8 hours at 50° to 60°C. At the end of this period the reaction mixture contained an insoluble organic material.

This material was separated and the trace amounts of solvent stripped under reduced pressure.

A viscous liquid weighing 5.2 g. was obtained. The I.R. indicated that the desired product was obtained.

EXAMPLE XIII

Preparation of Di-(2,2-di-(t-butylperoxy)-propyl) Sebacate[I]

A 100 ml jacketed reactor was charged with 4.94 g (0.0157 mole) of di(2-oxopropyl) sebacate, 9.3 g (0.0942 mole) of 91.3% t-butyl hydroperoxide and 50 ml of methylene chloride. To the resulting solution at 0°C was added 40 g of 77% $H_2SO_4$ over a period of 3 minutes (2° to 3°C exotherm) and the mixture was stirred for 4 hours at 0°C. After separation of the lower $H_2SO_4$ layer the product solution was washed with water, then with 50 ml of 5% $NaHSO_3$ solution and then with saturated NaCl solution to neutral. After drying over 5% by weight of anhydrous $MgSO_4$ and separation of the desiccant by filtration the methylene chloride was removed in vacuo thus giving 7.4 g of liquid which had an "active oxygen" content of 7.76% (10.02%, theory). The assay of the product was 77.4% and the corrected yield was 57.3%. An infrared spectrum of the product showed a single carbonyl band at 1740 $cm^{-1}$ (-which correponded to the ester groups) and an O—O band at 870 $cm^{-1}$.

The di-(2-oxopropyl) sebacate reactant was prepared by charging a closed 1000 ml flask with 37.1 g. (0.5 mole) of hydroxy-acetone, 37.0 g (0.44 mole) of pyridine and 200 ml of benzene. To this stirred solution at 25° to 30°C was slowly added 47.8 g (0.2 mole) of sebacoyl chloride and after the addition the mixture was stirred for 5 hours at 25° to 30°C. The pyridine hydrochloride (solid) was then separated by filtration and the resulting solution was washed once with 50 ml of water, twice with 50 ml of 10% $H_2SO_4$ and then with water to neutral. The product solution was then dried over 5% by weight of anhydrous $MgSO_4$, the desiccant was separated by filtration and the benzene was removed in vacuo thus giving a paste as a product. An infrared spectrum of the product indicated that compounds with carboxylic acid groups were present, therefore, the product was dissolved in 200 ml of benzene and the resulting solution was washed three times with 100 ml portions of 10% NaOH solution and then with water to neutral. After drying the solution over anhydrous $MgSO_4$ and separation of the desiccant by filtration the benzene was removed in vacuo. Obtained was 24.3 g (38.6% yield) of solid (m.p. 58°–61°C). An infrared spectrum of the product showed a ketone carbonyl band at 1725 $cm^{-1}$ and an ester carbonyl band at 1745 $cm^{-1}$, thus confirming the structure of the desired compound.

EXAMPLE XIV

Preparation of 2,4-Di-[2-methyl-3,3-di(t-butylperoxy) butoxycarbonylamino]toluene [II]

A 100 ml flask equipped with condenser, thermometer, drying tube and magnetic stirring bar was charged with 2.5 g (0.0142 mole) of tolylene-2,4-diisocyanate, 7.7g. (0.0291 mole) of 1-hydroxy-2-methyl-3,3-di(t-butylperoxy) butane and 35 ml of cyclohexane. The solution was cooled to 10°C and 0.2 g of dibutyltin diacetate was added and the mixture was heated to and held at 65°C for 4 hours. Then the mixture was agitated at 25° to 30°C for 16 hours after which 50 ml of diethyl ether was added. The resulting mixture was then washed with 50 ml of water, then with 50 ml of 10% NaOH solution and then with water to neutral. The solution was then dried over 5% by weight of anhydrous $MgSO_4$ and the desiccant was separated by filtration. The volatiles were then removed in vacuo thus giving a sticky glasslike product. For ease of handling 8.0 g of xylene was added. Obtained was 15.4 g of solution which had a diperoxyketal active oxygen content of 5.70% (9.10%, theory). The assay was 62.6% and the corrected yield was 96.4%. An infrared spectrum of the product solution showed urethane NH band at 3300 $cm^{-1}$, a urethane carbonyl band at 1710 $cm^{-1}$ and a O—O band at 875-880 $cm^{-1}$. There was no band in the infrared spectrum for the N=C=O group (at about 2200 $cm^{-1}$), hence, the product was not contaminated with isocyanate impurities.

The 1-hydroxy-2-methyl-3,3-di(t-peroxy)butane reactant was prepared by charging a 500 ml jacketed reactor with 19.5 g (0.19 mole) of 4-hydroxy-3-methyl-2-butanone, 112.5 g (1.14 moles) of 91.3% t-butyl hydroperoxide, 150 ml of pentane and 150 ml of methylene chloride. To the stirred solution at 0°C was slowly added 30.0 g of 77% $H_2SO_4$ over a period of 15 minutes and the resulting mixture was stirred for 4 hours at 0°C. The $H_2SO_4$ layer was then separated and the organic layer was washed with water to neutral. Then the organic layer was washed twice with 250 ml portions of 10% NaOH solution, then with 250 ml of water, then with 250 ml of 10% $NaHSO_3$ solution and finally with water to neutral. The solution was dried over 5% by weight of anhydrous $MgSO_4$ and the desiccant was separated by filtration. The volatiles were removed in vacuo leaving 21.5 g of liquid which had a diperoxyketal active oxygen content of 12.97% (12.10%, theory). The assay was 100% and the corrected yield was 43%. An infrared spectrum of the product showed an OH band at about 3400 $cm^{-1}$ and a very strong O—O band at about 875 $cm^{-1}$.

EXAMPLE XV

Crosslinkable Compositions

A mixture of the desired polymeric material and 0.01 mole of the difunctional coupled compound is blended together on a standard roll mill, such as used in the rubber industry. The mixture is removed from the roll mill and a portion is placed in a press mold and heat cured at a determined temperature for a period of 20 minutes.

The slabs are permitted to cool down and mature at room temperature for 24 hours. The mature slabs were then cut into dumbell shaped samples and tested for tensile strength on an Instron Tensile Tester, following ASTM procedure as described in D412-61T "Tension Testing of Vulcanized Rubber" or the crosslinking in the case of Polyethylene is determined by the solvent extraction procedure. In addition to the polymer-peroxide mixture, the crosslinkable mixture may contain co-agents such as sulfur, promoters, fillers and reinforcing materials. Desirable fillers are carbon black, titanium dioxide, calcium silicate and alkaline earth metal carbonates.

In Table I the crosslinking ability of the coupled compounds of our invention in polyethylene are compared to a hydroxy-containing peroxide and to difunctional peroxides. Tables II, III, and IV show the versatility of the product of our invention in urethane rubber, ethylene-propylene rubber and silicone rubber. The polyethylene used for the test in Table I was a low-density polyethylene called Bakelite DYNH-1, having the following physical properties:

Melt Index (ASTM Test D-1238)—190°C., 2.0 g./10 min.

Density (ASTM Test D-1505) — 0.919, and the crosslinking test was carried out at 340° and 375°F. for 30 minutes.

The urethane rubber formulation used in Table II was:

| | |
|---|---|
| Genthane - S | 100 parts |
| H.A.F. Carbon Black | 25 parts |
| Stearic acid | 0.2 parts |

Genthane-S is a designation given to one of the polyurethane elastomers developed by the General Tire & Rubber Company, having the following properties:

| | |
|---|---|
| Mooney Viscosity (ML4' 212°F.) | 50 ± 10 |
| Specific Gravity | 1.19 |

H.A.F. Carbon Black is a high abrasion furnace black. The urethane rubber charge without peroxide has 0 to 100 psi 300% modulus. The cure was carried out with 0.010 mole equivalent of peroxide at 340°F. for 30 minutes.

The ethylene-propylene rubber formulation used in Table III was:

| | |
|---|---|
| EPR-404 (an ethylene-propylene copolymer elastomeric material manufactured by Enjay, having specific gravity (g/cc) of 0.86 and Mooney Viscosity at 212°F., 8 minutes, of 40) | 100 parts |
| S.R.F. Carbon Black (a semi-reinforcing furnace carbon black manufactured by Cabot Corporation) | 60 parts |
| Sulfur | 0.33 part |
| Peroxide | 0.010 mole equivalent |
| Cure Time | 30 minutes |
| Cure Temperature | 340°F. |

Without peroxide, ethylene-propylene rubber copolymer has a 300% Modulus of 0 to 100 psi.

Table I

| | | | |
|---|---|---|---|
| | Crosslinking of Polyethylene | | |
| Peroxides | Molar Equivs. (2) | % Crosslinking (1) 340°F. | 375°F. |
| Di[1,3-dimethyl-3-(t-butylperoxy)butyl]carbonate (Examples I, II, & III) | 0.010 | 89.3 | 89.7 |
| Di[1,3-dimethyl-3-(t-butylperoxy)butyl]succinate (Examples VII) | 0.010 | 88.9 | 89.2 |
| Ethylene bis[1,3-dimethyl-3-(t-butylperoxy)-butyl carbonate] (Example VIII) | 0.010 | 87.9 | 87.4 |
| 2-Methyl-2-(t-butylperoxy)-4-pentanol | 0.015 | 78.4 | 75.4 |
| 2,5-dimethyl-2,5-di(t-butylperoxy)-hexane | 0.010 | 85.9 | 84.5 |
| 2,5-dimethyl-2,5-di(t-butylperoxy)-hexyne-3 | 0.010 | 81.8 | 84.9 |

Table I-continued

Crosslinking of Polyethylene

| Peroxides | Molar Equivs. (2) | % Crosslinking (1) 340°F. | 375°F. |
|---|---|---|---|
| 2,5-dimethyl-2,5-di(t-butylperoxy)-hexane | 0.015 | 89.3 | 88.0 |
| 2,5-dimethyl-2,5-di(t-butylperoxy)-hexyne-3 | 0.015 | 86.0 | 87.7 |

(1) The percentage crosslinking was determined by extraction of the crosslinked sample with refluxing xylene. In all cases the polyethylene charge was 100% extractable before crosslinking.
(2) Based on number of active oxygens per mole.

From the table it is obvious that the coupled compounds of our invention are more efficient than the hydroxy containing peroxide that they were derived from. This test also shows that the coupled compounds are significantly more efficient at equal molar equivalents than other difunctional peroxides that are commercially used to crosslink polyethylene.

TABLE II

VULCANIZATION OF URETHANE RUBBER FORMULATION

| Peroxides | (psi) 300% Modulus | (psi) Ult. Tensile | (psi) % Elongation |
|---|---|---|---|
| Di[1,3-dimethyl-3-(t-butylperoxy)butyl]carbonate (Examples I, II, and III) | 2091 | 4512 | 493 |
| Di[1,3-dimethyl-3-(t-butylperoxy)butyl]succinate (Example VII) | 1472 | 4167 | 575 |
| Ethylene bis[1,3-dimethyl-3-(t-butylperoxy) butyl carbonate] (Example VIII) | 2419 | 3502 | 375 |

TABLE III

VULCANIZATION OF ETHYLENE-PROPYLENE RUBBER FORMULATION

| Peroxides | (psi) 300% Modulus | (psi) Ult. Tensile | (psi) % Elongation |
|---|---|---|---|
| Di[1,3-dimethyl-3-(t-butylperoxy)butyl] carbonate (Examples I, II, and III) | 1004 | 2118 | 567 |
| Di[1,3-dimethyl-3-(t-butylperoxy)butyl] succinate (Example VII) | 715 | 2096 | 710 |
| Ethylene bis[1,3-dimethyl-3-(t-butylperoxy) butyl carbonate] (Example VIII) | 1089 | 2232 | 552 |

TABLE IV

CROSSLINKING OF SILICONE RUBBER FORMULATION

| | | |
|---|---|---|
| Silicone Rubber-404 (1) | | 100 parts |
| Peroxide | | 0.010 mole equivalents |
| Cure Temperature | | 340°F. |
| Cure Time | | 30 minutes |

| Peroxides | (psi) 300% Modulus | (psi) Ult. Tensile | (psi) % Elongation |
|---|---|---|---|
| Di[1,3-dimethyl-3-(t-butylperoxy)butyl] carbonate (Examples I, II, & III) | 478 | 871 | 431 |

(1) Silicone Rubber-404 is a general purpose reinforced silicone gum manufactured by General Electric. The silicone rubber charge without peroxide has a 300% modulus of 0 psi.

EXAMPLE XVI

This example illustrates the use of coupled peroxides of the present disclosure as initiators of vinyl monomer polymerization. Compound [B] (from Example V) at a concentration of $5 \times 10^{-4}$ moles per deciliter of styrene, polymerized styrene at 100°C. at a rate of $6.20 \times 10^{-3}$ moles per liter per minute. When no initiator is present, the thermal polymerization of styrene at 100°C. proceeds at a rate of $2.82 \times 10^{-3}$ moles per liter per minute. Compound [A] (from Examples I, II, and III) at a concentration of $5 \times 10^{-4}$ moles per deciliter of styrene polymerized styrene 1.65 times faster at 115°C. than the thermal polymerization rate when no polymerization initiator is present.

EXAMPLE XVII

Curing An Unsaturated Polyester-Styrene Resin With Coupled Peroxide

A. An unsaturated polyester resin was made by reacting maleic anhydride (1.0 mole), phthalic anhydride (1.0 mole), and propylene glycol (2.2 mole) until an acid number of 45–50 was obtained. To this was added hydroquinone at a 0.013% concentration. Seven parts of this unsaturated polyester was diluted with 3 parts of monomeric styrene to obtain a homogeneous blend having a viscosity of 13.08 poise and a specific gravity of 1.14. To 20 g. of this blend was added the 0.2 g. of the desired coupled peroxide and the resulting composition placed in a constant temperature bath at 115°C.

The internal temperature was recorded as function of time. The following results were obtained with some of the coupled compounds (Table V):

TABLE V

S. P. I. EXOTHERM AT 115°C. AND 1% CONCENTRATION IN POLYESTER RESIN

| Peroxides | Gel Time In Min. | Cure Time In Min. | Peak In °F | Barcol Hardness |
|---|---|---|---|---|
| Di[1,3-dimethyl-3-(t-butylperoxy)-butyl] carbonate (Examples I, II, and III) | 9.5 | 11.1 | 455 | 45 |
| Ethylene bis[1,3-dimethyl-3-(t-butylperoxy)butyl carbonate] (Example VIII) | 10.8 | 12.8 | 450 | 45 |
| Di[2-(t-butylperoxycarbonyl)ethyl] carbonate (Example V) | 7.1 | 8.5 | 450 | 45 |

Without an initiator, no cure of this resin blend occurred after more than 30 minutes at 115°C.

B. Cure characteristics of compounds I and II of Examples XIII and XIV compared to those of t-butyl peroxybenzoate (a standard curing agent used commercially in curing of unsaturated polyester resins) were determined in the unsaturated polyester resin of part (A) of this example. Gelation and cure characteristics were determined using the standard SPI Exotherm Procedure ("SPI Procedure for Running Exotherm Curves—Polyester Resins," published in the Preprint of the 16th Annual Conference — Reinforced Plastics, Division of the Plastics Industry, Inc., February 1961). Using this procedure at 115°C, (I), (II) and t-butyl peroxybenzoate were employed to cure the standard unsaturated polyester resin. The level of catalyst employed was 1% by weight of pure peroxide. The 115°C SPI Exotherm data for these peroxides are given in Table V(B) and show that the peroxides of

TABLE V (B)

| | 115°C SPI Exotherms | | | |
|---|---|---|---|---|
| Peroxide | Gel., Mins. | Cure, Mins. | Peak, °F | Barcol Hardness |
| (I) | 3.1 | 4.0 | 452 | 40 |
| (II) | 2.6 | 3.6 | 448 | 40–45 |
| t-Butyl Peroxybenzoate | 4.1 | 5.0 | 446 | 40–45 | this invention are more active on a weight basis than t-butyl peroxybenzoate.

EXAMPLE XVIII

Half-Life Comparisions of Coupled and Uncoupled Hydroxy-Peroxides (Carried out in Benzene at 0.1 molar concentrations)

| Peroxide | $t_{1/2}$ Hours (°C) |
|---|---|
| 2-Methyl-2-(t-butylperoxy)-4-pentanol | 13.6 (115°C.) |
| Di[1,3-dimethyl-3-(t-butylperoxy)butyl] carbonate (Examples I, II, & III) | 26.8 (115°C.) |
| t-butylperoxy 3-hydroxypropionate | 13.0 (100°C.) |
| Di(2-(t-butylperoxycarbonyl)ethyl] carbonate (Example V) | 30.7 (100°C.) |

As can be seen from the half-life values, the peroxides containing hydroxyl have significantly lower half-lives than the coupled compounds. Thus, the coupled peroxides are more thermally stable and safer to handle, ship, store and use.

Thus having described the invention, what is claimed is:

1. A compound of the formula R—C(=O)—R$^4$—C(=O)—R' where:
   a. R and R' are identical and are selected from
      R$_3$—OO—C(R$_1$)(R$_2$)—R$^3$—O—,
      (R$_3$—OO—)$_2$C(R$_4$)—R$^2$O—, R$_3$—OO—C(=O)—R$^3$O—, R$_3$OO—C(=O)—OR$^3$O—, R$_1$OC(=O)—OO—C(R$_1$)(R$_2$)—R$^2$O— and
      R$_1$C(=O)—OO—C(R$_1$)(R$_2$)—R$^2$O—;
   b. R$_1$ and R$_2$ are C$_1$ — C$_{12}$ hydrocarbon aliphatic;
   c. R$_3$ is C$_4$—C$_{10}$ hydrocarbon aliphatic and the carbon atom joined to the peroxy oxygen atom is a tertiary carbon;
   d. R$_4$ is C$_1$—C$_{10}$ hydrocarbon aliphatic;
   e. R$_6$ is H or lower alkyl;
   f. Y is —N(R$_6$)—;
   g. R$^2$ is C$_1$—C$_{10}$ hydrocarbon aliphatic;
   h. R$^3$ is C$_1$—C$_{10}$ hydrocarbon aliphatic, C$_3$—C$_{12}$ hydrocarbon cycloaliphatic or C$_6$—C$_{12}$ hydrocarbon aromatic, with the proviso the R$^3$ is not aromatic when R$^4$ is R$^3$; and
   i. R$^4$ is R$^3$, YR$^3$Y, YR$^3$OC(=O)R$^3$C(=O)OR$^3$Y, YR$^3$OC(=O)R$^3$Y or YR$^3$OR$^3$Y.

2. A compound of claim 1 wherein R$^4$ is R$^3$.

3. A compound of claim 2, di(1,3-dimethyl-3-(t-butylperoxy)butyl)succinate.

4. A compound of claim 1, N,N'-m-phenylene bis (1,3-dimethyl-3-(t-butylperoxy)butyl carbamate).

5. A compound of claim 1, bis(2-(1,3-dimethyl-3-(t-butylperoxy)-butoxycarboxamido) ethyl) fumarate.

* * * * *

UNITED STATES PATENT OFFICE
CERTIFICATE OF CORRECTION

Patent No. 3,965,145     Dated June 22, 1976

Inventor(s) Antonio Joseph D'Angelo    Orville Leonard Mageli
            Chester Stephen Sheppard It is certified that error appears in the above-identified patent and that said Letters Patent are hereby corrected as shown below:

Claim 1

Line 26 to Line 46 b.   $R_1$ and $R_2$ are $C_1$ - $C_{12}$ hydrocarbon aliphatic;

c.   $R_3$ is $C_4$ - $C_{10}$ hydrocarbon aliphatic and the carbon atom joined to the peroxy oxygen atom is a tertiary carbon;

d.   $R_4$ is $C_1$ - $C_{10}$ hydrocarbon aliphatic;

e.   $R_6$ is H or lower alkyl;

f.   Y is $-N(R_6)-$;

g.   $R^2$ is $C_1$ - $C_{10}$ hydrocarbon aliphatic;

h.   $R^3$ is $C_1$ - $C_{10}$ hydrocarbon aliphatic, $C_3$ - $C_{12}$ hydrocarbon cycloaliphatic or $C_6$ - $C_{12}$ hydrocarbon aromatic, with the proviso the $R^3$ is not aromatic when $R^4$ is $R^3$, and

SHOULD READ b.   $R_1$ and $R_2$ are $C_1$-$C_{12}$ alkyl, $C_3$ - $C_{12}$ cycloalkyl or $C_6$ - $C_{12}$ aromatic;

c.   $R_3$ is $C_4$ - $C_{10}$ alkyl, cycloalkyl or aralkyl and the carbon atom joined to the peroxy oxygen atom is a tertiary carbon;

d.   $R_4$ is $C_1$ - $C_{10}$ alkyl and $C_3$ - $C_{12}$ cycloalkyl;

Continuation - Certificate of Correction
3,965,145
June 22, 1976
Antonio Jospeh D'Angelo   Orville Leonard Mageli
Chester Stephen Sheppard e. $R_6$ is H or lower alkyl;

f. Y is $-N(R_6)-$;

g. $R^2$ is $C_1 - C_{10}$ alkyl and $C_3 - C_{12}$ cycloalkyl diradical;

h. $R^3$ is $C_1 - C_{10}$ hydrocarbon aliphatic, $C_3 - C_{12}$ cycloalkyl or $C_6 - C_{12}$ hydrocarbon aromatic, with the proviso that $R^3$ is not aromatic when $R^4$ is $R^3$; and

Signed and Sealed this

Second Day of November 1976

[SEAL]

Attest:

RUTH C. MASON
*Attesting Officer*

C. MARSHALL DANN
*Commissioner of Patents and Trademarks*